United States Patent [19]

Stoler et al.

[11] Patent Number: 5,912,147
[45] Date of Patent: Jun. 15, 1999

[54] RAPID MEANS OF QUANTITATING GENOMIC INSTABILITY

[75] Inventors: Daniel Stoler, Getzville, N.Y.; Mark Basik, Pierrefonds, Canada; Garth Anderson, Elma, N.Y.

[73] Assignee: Health Research, Inc., Buffalo, N.Y.

[21] Appl. No.: 08/734,973

[22] Filed: Oct. 22, 1996

[51] Int. Cl.⁶ .............................. C12P 19/34; C12Q 1/68; C07H 21/04

[52] U.S. Cl. ..................... 435/91.2; 435/6; 536/24.33; 935/8; 935/77; 935/78

[58] Field of Search ................................ 435/6, 91.2, 810; 536/22.1, 24.1, 24.3, 24.31, 24.33; 935/8, 77, 78

[56] References Cited

PUBLICATIONS

Zietkiewicz et al., "Genome Fingerprinting by Simple Sequence Repeat (SSR)–Anchored Polymerase Chain Reaction Amplification", 1994, Genomics, vol. 20, pp. 176–183.

Cross et al. "CpG islands & genes" Current Biology 5:309–314 (Jun. 1995).

Makos et al. Proc.Natl.Acad. USA. 89:1929–1933 (Mar. 1992).

Sheardy. Nucl.Acids. Res. 16:1153–1167 (Feb. 1988).

*Primary Examiner*—W. Gary Jones
*Assistant Examiner*—Debra Shoemaker
*Attorney, Agent, or Firm*—Hodgson, Russ, Andrews, Woods & Goodyear

[57] ABSTRACT

Provided is a method for detecting genomic instability, independent of microsatellite alterations, comprising the steps of treating a comparison pair of genomic DNA from tumor cells and genomic DNA from normal cells with oligonucleotide primers under conditions for, and in an amplification reaction to, amplify a target sequence associated with such genomic instability. Detection of an alteration in the banding pattern of amplified product from genomic DNA from tumor cells as compared to that of normal cells, is indicative of such genomic instability. Additionally provided is a process for simultaneously assessing changes in methylation patterns in the genomic DNA tested comprising treating the genomic DNA with reagents for detecting methylation status prior to the amplification reaction, comparing the resultant banding patterns of amplified products, wherein differences in the banding patterns is indicative of an alteration in methylation. Disclosed are novel compositions for use in a method for detecting genomic instability, independent of microsatellite alterations.

15 Claims, 8 Drawing Sheets

FIG. IA
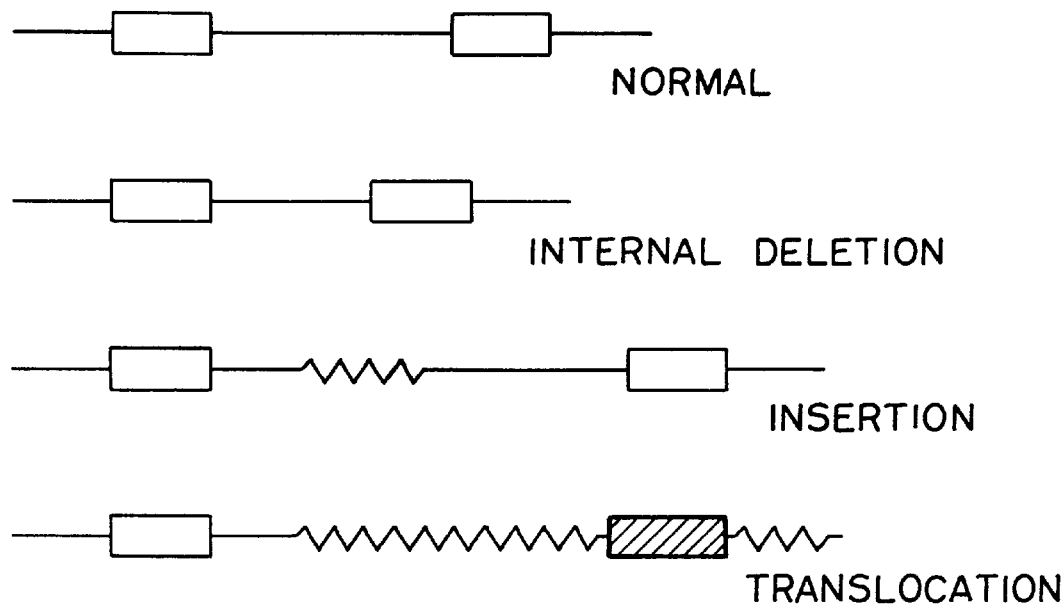
FIG. IB
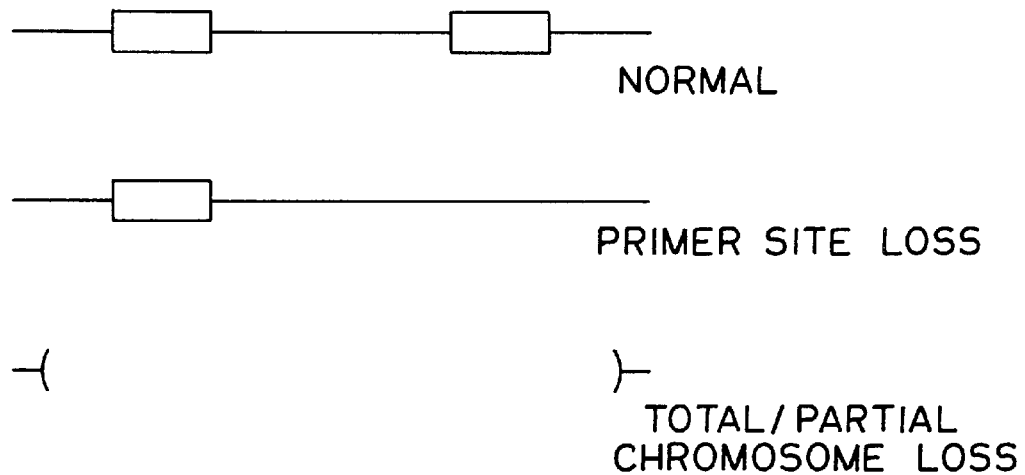
FIG. IC
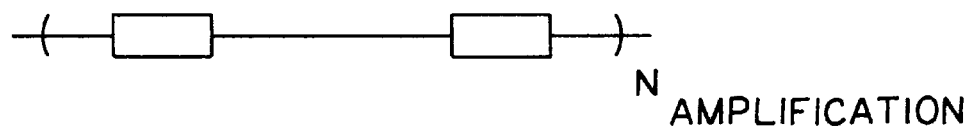

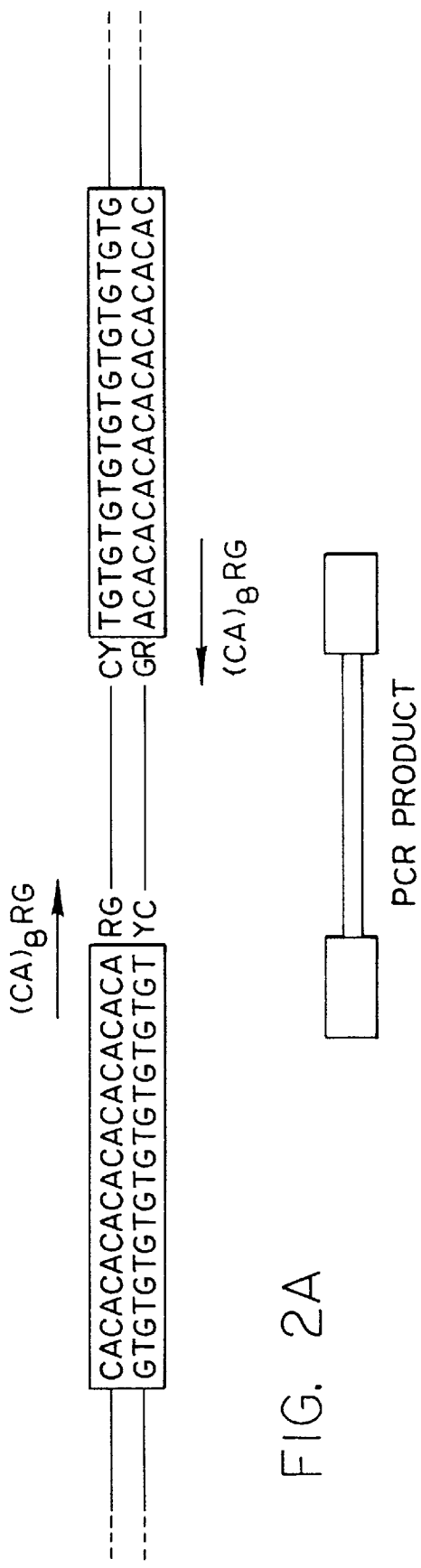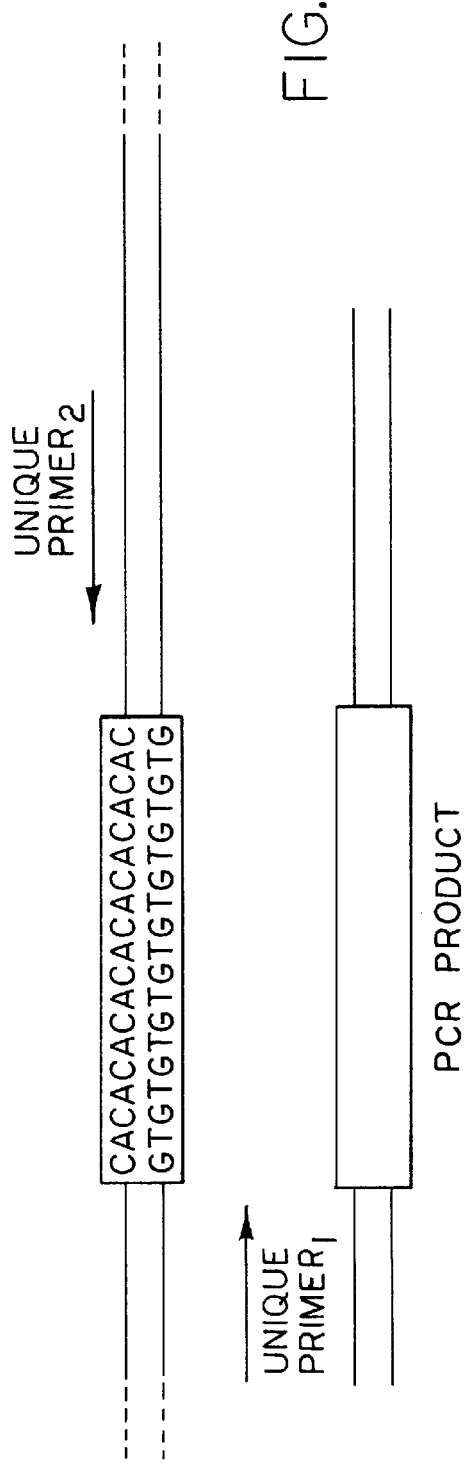
FIG. 2A
FIG. 2B

RAPID MEANS OF QUANTITATING GENOMIC INSTABILITY

FIELD OF THE INVENTION

The present invention relates to the fields of molecular biology and oncology, and provides novel compositions and methods for detection of genomic instability. More particularly, the present invention relates to genetic testing with novel compositions in providing a rapid method for quantitating genomic instability of tumors.

BACKGROUND OF THE INVENTION

Cancer is "a disease of genetic instability" (National Cancer Institute Director Richard Klausner, as quoted in Science 273:1329, 1996). The process of carcinogenesis is believed to require multiple genetic and/or epigenetic events which affect patterns of expression, or result in mutational alteration, of genes. Various molecular mechanisms may be responsible for the DNA mutation and genetic instability leading to the development of tumorigenesis. Such molecular mechanisms include DNA damage and mutation, alteration of a cell's ability to repair damaged or mutated DNA, alteration of genes responsible for cell-cycle control mechanisms, and alteration of protooncogenes or tumor suppressor genes. However, additional other unknown mechanisms for genetic instability also exist.

DNA damage can result from spontaneous alteration of the DNA molecule, such as a mutation caused during DNA replication, DNA repair, gene rearrangement, or chemical alteration as a result of oxidation or methylation. DNA damage can also result from interaction between the DNA molecule with physical agents (e.g., ionizing radiation); and with chemical agents (e.g., cross-linking agents). A individual gene's degree of sensitivity to DNA damaging agents depends on factors such as the sequence of the gene, and whether it is being actively transcribed or replicated.

There are several pathways by which DNA damage may be repaired (e.g., nucleotide excision repair, enzymatic reversal repair, and postreplication repair). Defects in DNA repair mechanisms may include either somatic or germline mutation of genes encoding proteins necessary for DNA repair and maintenance of genome stability. A defect in DNA repair may accelerate the accumulation of mutations in genes critical to maintain homeostasis, contributing to genomic instability and malignant transformation.

Proliferation of normal cells is associated with protooncogene expression, whereas tumor suppressor genes function in the negative regulation of cell proliferation. Mutations of cellular protooncogenes and tumor suppressor genes could fix a cell in a state of uncontrolled proliferation that could contribute to the development of genomic instability by allowing for replication of damaged DNA before a DNA repair process is complete. Accumulation of a critical number of DNA mutations (genomic instability) can ultimately result in neoplastic transformation.

Genomic instability is believed to occur in an early step in the process of carcinogenesis. Phenotypic changes, directly or indirectly resulting from genomic instability, observed in the progression during neoplastic transformation are used in the diagnosis, staging, and prognosis of malignancies. Thus, a means for detecting and quantitating genomic instability has applications in the diagnosis, staging, and monitoring of cancer patients. Further, therapeutic choices, modalities, and strategies may depend on the accurate assessment of the stage of malignant disease. There are several different manifestations or patterns of genomic instability which have been used successfully in examination of human tumors: abnormal karyotype; increased copy number of genes or of specific nucleotide sequences affecting gene expression; and microsatellite instability.

Microsatellite instability thus represents only one specific manifestation of genomic instability. Microsatellite instability is represented by an alteration in size of microsatellite (simple repeat) sequences. A finding of microsatellite instability represents mutations in one or more genes involved in DNA mismatch repair mechanisms. Thus, while methods for detecting microsatellite instability are important tools in genetic testing of some tumors (e.g., hereditary nonpolyposis colorectal cancer), such methods do not detect major form(s) of genomic instability characterized by molecular aneuploidy arising from deletions, amplifications, translocations, insertions, recombination, and chemical alteration (See FIGS. 1A–1C). For example, microsatellite analysis only specifically detects a subset of colorectal cancers (Bocker et al., 1996, J. Pathol. 179:15–19); of nonsmall cell lung carcinoma (Wieland et al., 1996, Oncol. Res. 8:1–5), and appears not to be particularly useful for small cell lung carcinoma (Adachi et al., 1995, Genes Chromosomes Cancer 14:301–306), for lymphoid neoplasia (Volpe et al., 1996, Ann. Hematol. 72:67–71) or for bone tumors (Tarkkanen et al., 1996, Br. J. Cancer 74:453–5), suggesting a role for other forms of genomic instability in these tumor types.

Accordingly, there is a need in this art for novel, rapid, relatively inexpensive methods and compositions for molecular screening of tumors in quantitating forms and patterns of genomic instability other than the pattern represented by microsatellite instability.

SUMMARY OF THE INVENTION

Measurement of genomic instability, other than the pattern represented by microsatellite instability, may be made by a variety of techniques including flow cytometry, comparative genomic hybridization, allelotyping, analysis of gene amplification rates, and gene sequencing. Such approaches, although informative, are generally cumbersome and somewhat impractical for widespread clinical use. The present invention relates to the development of a rapid and simple technique termed "inter-simple sequence repeat amplification reaction" (hereinafter referred to as "inter-SSR PCR"), and novel compositions useful therewith, for conveniently detecting and measuring common genetic events of genomic instability independent of instability observed from DNA mismatch repair defects (i.e., microsatellite alterations). Additionally, in an embodiment in which a modification of the method according to the present invention is used, changes in methylation patterns that may affect transcriptional activity of genes adjacent to the change can be assessed as well as genomic instability.

Thus, one object of the invention is to provide a method for detecting genomic instability, independent of microsatellite alterations, comprising the steps of treating genomic DNA with a composition (oligonucleotide primers) under conditions for, and in an amplification reaction to, amplify a target sequence associated with such genomic instability, wherein detection of an alteration in the amplified target sequence from genomic DNA from abnormal cells (e.g. tumor cells) but not in normal cells, is indicative of such genomic instability.

Another object of the invention is to provide a method for detecting genomic instability, independent of microsatellite alterations, using a rapid and simple technique.

A further object of the present invention is to provide a method for detecting genomic instability, independent of microsatellite alterations, which simultaneously can assess changes in methylation patterns adjacent to genes contained in the genomic DNA tested.

An additional object of the present invention is to provide kits comprising compositions selected from the group consisting of oligonucleotide primers and ancillary reagents used in an amplification reaction in a method for detecting genomic instability, independent of microsatellite alterations, which can simultaneously assess genomic instability and changes in methylation patterns adjacent to genes contained in the genomic DNA tested.

Other objects, features, and advantages of the present invention will become apparent from the following drawings and detailed description.

BRIEF DESCRIPTION OF THE DRAWINGS

FIGS. 1A–1C is an illustration of forms and patterns of genomic instability, other than the pattern represented by microsatellite instability, detected by the method according to the present invention.

FIGS. 2A–2B is an illustration comparing genomic sequences located between $(CA)_n$ microsatellite sequences as amplified by the method according to the present invention, and amplified microsatellite sequences.

DETAILED DESCRIPTION OF THE INVENTION

Definitions

Figure 3:
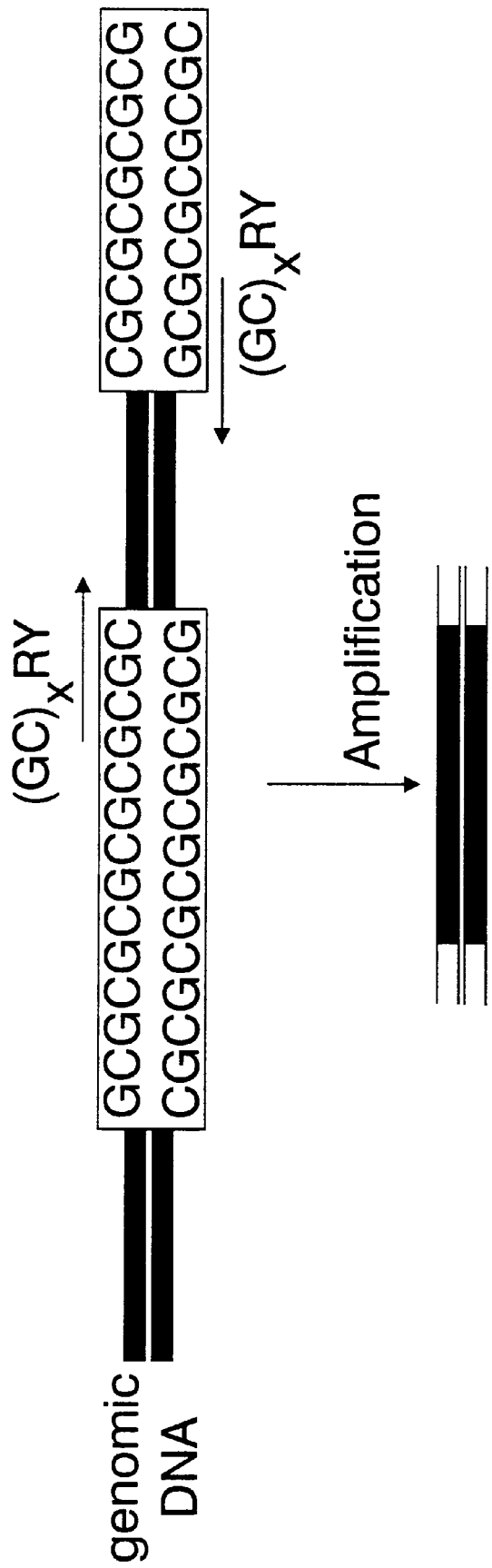
FIG. 3 is an illustration of amplification of sequences between CpG islands, as primed with CpG island homologous sequences.

By the term "consisting essentially of" or "consisting of" a nucleotide sequence is meant, for the purposes of the specification or claims, the nucleotide sequence disclosed, and also encompasses nucleotide sequences which are identical except for a base change or substitution therein. As known to those skilled in the art a limited number of base changes or substitutions may be made in a short oligonucleotide sequence resulting in a sequence still maintaining function substantially (ranging from approximately 50% of the activity to greater than 100% of the activity) of the original unmodified sequence.

By the term "individual" is meant, for the purposes of the specification and claims to refer to any mammal, especially humans.

By the term "genomic instability" is meant, for the purposes of the specification and claims to refer to any condition, caused by a genetic or epigenetic event, that predisposes a cell to accumulation of stable DNA mutations or alterations at a greater rate than normally encountered in that cell type. In mammalian cells, genomic instability, in a state whereby DNA damage/alteration/mutation has accumulated, can lead to neoplastic transformation.

By the term "genomic instability index" is meant, for the purposes of the specification and claims, to refer to a measure of the number of alterations in tumor DNA in comparison with DNA of normal cells, expressed as a percent, and detected by a method according to the present invention. For example, as determined from the banding pattern of amplified DNA, the genomic instability index= (number of altered bands/total number of normal bands)× 100.

By the term "microsatellite instability" or "microsatellite analysis" is meant, for the purposes of the specification and claims to refer to the measurement or detection of alterations in microsatellite sequences which are known by those skilled in the art to represent a specific pattern of genomic instability caused by DNA mismatch repair defects. Alterations in microsatellites (microsatellite instability) have been clinically useful in various inherited diseases and in some types of cancer. Microsatellite sequences are short tandem repeat sequences ("microsatellites") that are broadly distributed in a genome. For example, the human genome is believed to contain >100,000 repeat regions. Microsatellites are thought to play a role in chromatin structure and nucleosome placement.

By the term "enzymatically amplify" or "amplify" or "amplification" is meant, for the purposes of the specification and claims, to refer to a process by which nucleic acid sequences are amplified in number. There are several means known well to those skilled in the art for enzymatically amplifying nucleic acid sequences (see, e.g. a review in Bio/Technology 8:290–3, 1990). Currently the most commonly used method, PCR (polymerase chain reaction) involves the use of a thermostable DNA polymerase, known sequences as primers, and heating cycles which separate the replicating deoxyribonucleic acid (DNA) strands and exponentially amplify a nucleotide sequence of interest ("target sequence"). Other amplification methods include LCR (ligase chain reaction) which utilizes DNA ligase, and a probe consisting of two halves of a DNA segment that is complementary to the sequence of the DNA to be amplified; enzyme QB replicase and a ribonucleic acid (RNA) sequence template attached to a probe complementary to the DNA to be copied which is used to make a DNA template for exponential production of complementary RNA; and NASBA (nucleic acid sequence-based amplification) which can be performed on RNA or DNA as the nucleic acid sequence to be amplified. This invention is not limited to any particular amplification system, as other systems developed may benefit by the practice of this invention.

By the term "detectable label" or "label" is meant, for the purposes of the specification or claims, a molecule (isotopic or non-isotopic) which is incorporated indirectly or directly into an oligonucleotide primer or the amplified product. For example, the label molecule facilitates the detection of the oligonucleotide in which it is incorporated when the oligonucleotide becomes part of the amplified DNA sequences. Synthesis of oligonucleotides can be accomplished by any one of several methods known to those skilled in the art. To incorporate a label into an oligonucleotide, the label may be added in the form of a deoxynucleoside triphosphate (dNTP) containing the label, and then the dNTP may be added in the process of synthesizing the oligonucleotide, so that the label is incorporated directly into the oligonucleotide (See for example, *Molecular Cloning*, a laboratory manual: editors Sambrook, Fritsch, Maniatis; Cold Spring Harbor Laboratory Press, 1989). Alternatively, the label may be incorporated "indirectly" such as, for example, by coupling a primer at the 5'end with an aminohexyl linker using a standard DNA synthesis cycle, and subsequently coupling to the oligonucleotide via the linker a fluorescent dye-NHS ester. Various fluorescent molecules are known in the art which are suitable for use to label a nucleic acid substrate for the method of the present invention. Fluorescent molecules used as labels may include amine-reactive molecules which are reactive to end terminal amines of the substrate; sulfonyl chlorides which are conjugated to the substrate through amine residues; and the like. Depending on the fluorescent molecule used, incorporating the substrate with the fluorescent molecule label include attachment by covalent or noncovalent means. The protocol for such incorporation may vary depending upon the fluorescent molecule used. Such protocols are known in the art for the respective fluorescent molecule (see, e.g., Karnik et al., 1995, *Hum. Mol. Genet.* 4:1889–1894).

By the term "primer" or "oligonucleotide primer" is meant, for the purposes of the specification and claims, to refer to an oligonucleotide capable of acting as a point of initiation for DNA strand synthesis when annealed to a complementary sequence under suitable conditions and in the presence of nucleotide triphosphates for synthesis to occur.

By the term "sample" is meant, for the purposes of the specification and claims to refer to any body tissue or fluid suitable for detecting tumor cells, including, but not limited to biopsies, bone marrow or lymph node aspirates, effusions, ascites, cerebrospinal fluid, and peripheral blood.

Specific microsatellite markers, and primer pairs used to amplify and detect these polymorphisms, are disclosed in U.S. Pat. No. 5,378,602. Another technique for amplifying microsatellite sequences is genomic fingerprinting by inter-SSR PCR (Zietkiewicz et al., 1994, *Genomics* 20:176–183). The inter-SSR PCR reaction targeted tandemly repeated short sequences (microsatellites) of $(CA)_n$ repeats where n is a number typically between 10–60. For purposes of taxonomic and phylogenetic comparisons, these $(CA)_n$ repeats were utilized for amplification by using either 3'-anchored primers or 5'-anchored primers.

For 3'-anchored primers, two 18 nucleotide primers were synthesized: $(CA)_8RG$, wherein R is a purine selected from the group consisting of adenine and guanine (representative examples of these primers are shown as SEQ ID NO:1 & SEQ ID NO:2); and $(CA)_8RY$, wherein R is a purine selected from the group consisting of adenine and guanine, and Y is a pyrimidine selected from the group consisting of cytosine, thymine, and uracil (representative examples of these primers are shown as SEQ ID NOs:3–8). The RG or RY portion at the 3' end of the primer anchors the primer to sequences outside the microsatellite, thereby allowing initiation of synthesis from the primer by avoiding priming from within the $(CA)_n$ microsatellite. Subsequent amplification, and resolution by gel electrophoresis, results in the detection of genomic sequences that are flanked by the microsatellites, wherein the pattern of amplified sequences is used for species-specific fingerprints.

The 5'-anchored primers were designed to anchor in the 5' end of a microsatellite, and may be used to amplify microsatellite sequences for taxonomic and phylogentic comparisons. It was also suggested by Zietkiewicz et al., that the 5'-anchored primers could potentially be used in an inter-SSR PCR method for amplifying microsatellites to screen for somatic events in tumors (microsatellite instability) due to DNA mismatch repair defects. However, as described above in more detail, microsatellite instability represents a specific pattern of genomic instability. Microsatellite analysis would therefore not detect the major form of genomic instability, characterized by molecular aneuploidy arising from deletions, amplifications, translocations, insertions, and recombination (the common feature of which appears to be DNA strand breakage).

The inventors of the present invention hypothesized that the inter-SSR PCR technique might be useful in a method for detecting a major type of genomic instability if the technique could detect chromosomal (DNA) breaks in genomic sequences located between $(CA)_n$ microsatellite sequences versus the microsatellite sequences themselves (See FIGS. 2A–2B). In this first embodiment of the invention, it was an unexpected result that the resultant amplification revealed a high frequency of band alterations in tumors, compared to normal cells of the same tissue type from the same individual; and further, that a genomic instability index could be calculated from the frequency of band alterations thereby allowing the genomic instability index to be used as a clinical parameter. This first embodiment is illustrated in Examples 1–3 herein.

In a second embodiment of the invention, a more sensitive method was advanced by developing (CG)-based primers. According to this second embodiment, 3'-anchored primers were synthesized: $(CG)_xRG$, wherein R is a purine selected from the group consisting of adenine, guanine, and a combination thereof (a mixture of primers, some where R is adenine, some where R is guanine) and wherein x is a number from about 3 to 7, with a preferred number of about 4–5 (representative examples of these primers are shown as SEQ ID NOs:9–10); $(CG)_xRY$, wherein R is a purine selected from the group consisting of adenine, guanine, and a combination thereof, Y is a pyrimidine selected from the group consisting of cytosine, thymine, uracil, and wherein x is a number from about 3 to 7, with a preferred number of about 4 to 5 (representative examples of these primers are shown as SEQ ID NOs:11–16) ; $(CG)_xRR$, wherein R is a purine selected from the group consisting of adenine, guanine, and a combination thereof, and wherein x is a number from about 3 to 7, with a preferred number of about 4 to 5 (representative examples of these primers are shown as SEQ ID NOs:17–18); and $(CG)_xYY$, wherein Y is a pyrimidine selected from the group consisting of cytosine, thymine, and uracil, and wherein x is a number from about 3 to 7, with a preferred number of about 4 to 5 (representative examples of these primers are shown as SEQ ID NOs:1–27). These (CG)-based primers were unexpectedly effective and sensitive in scanning the genome for genomic instability, and for the overall frequency of methylation alterations (herein termed "methylation fingerprinting").

Unlike the (CA)-based primers, the (CG)-based primers amplify CG-rich regions termed "CpG islands" and the sequences between islands (See FIG. 3). The RG, RY, RR, and RY portions at the 3' end of the respective (CG)-based primer anchors the primer to sequences outside the CpG islands, thereby allowing initiation of synthesis from the primer by avoiding priming from within the CpG islands. Changes in methylation of CG-rich regions are known to be able to greatly influence transcriptional activity of genes adjacent to these regions. Further, the most frequent spontaneous chemical modification of the DNA molecule is the deamination of methylated cytosine residues in CpG islands, and this type of modification apparently accounts for a large percentage of spontaneous mutations in human disease (Cooper et al., 1988, *Hum. Genet.* 78:151–5). Deamination of 5-methylcytosine to thymine results in G:T mismatches (if left unrepaired, results in genomic instability), as well as a change in methylation pattern.

Using the method and compositions according to the second embodiment of the invention, amplified products can be generated from genomic DNA. The DNA molecules may be subjected to analysis by a reagent that detects methylation status. For example, some restriction enzymes are sensitive to methylation status (e.g., Hpa II will cut its recognition site if the site is unmethylated), while other restriction enzymes are not (e.g., Msp I will cut regardless of methylation status). Thus, band by band comparison, and comparison of DNA from normal cells, can thus reveal changes in overall methylation status (from which can be calculated a methylation index that may be useful in evaluating prognosis), while simultaneously assessing genomic instability.

As an example of the importance of the mutations in the CpG islands, it has been observed that the majority of point mutations in the p53 tumor-suppressor gene in human tumors are at codons that contain CpG sites. Specifically, codons 175, 248, and 273 are important in colorectal tumors; codon 213 is important in leukemias and lymphomas; and codons 196, 213, and 282 have been implicated in several tumor types (Hollstein et al., 1991, *Science* 253:49–53; Greenblat et al., *Cancer Res.* 54: 4855–78). Additionally, frequently chemical modification of the DNA molecule is of residues in CpG islands. For example, benzo[α]pyrene, a common chemical carcinogen, typically produces mutation of guanine to thymine, which affects nucleotides in GC-rich stretches of DNA (Eisenstadt et al., 1982, *Proc. Natl. Acad. Sci.* 79:1945–9). Thus, the method and compositions according to the second embodiment of the invention are particularly sensitive in detecting in a DNA molecule spontaneous mutations and mutations induced by chemical carcinogens, i.e., genomic instability other than the pattern represented by microsatellite instability. Using this method encompassed by the second embodiment of the present invention, a genomic instability index and/or methylation index could be calculated from the frequency of band alterations thereby allowing the genomic instability index and/or methylation index to be used as a clinical parameter. This second embodiment is illustrated in Examples 1 and 4 herein.

EXAMPLE 1

To illustrate an embodiment for the enzymatic amplification of the DNA sequences related to genomic instability, an inter-SSR PCR method was utilized. Generally, closely adjacent (e.g., less than 2 kilobases apart) repeat sequences arranged tail to tail will be optimally amplified by this technique. For the method of detecting chromosomal (DNA) breaks in genomic sequences located between $(CA)_n$ microsatellite sequences, $(CA)_xRG$ (where in a mixture of primers, R is a purine of approximately half in amount as adenine, and approximately half in amount as guanine; and wherein x is a number from about 6 to 16, with a preferred number of 8) (representative examples of these primers are shown as SEQ ID NOs:1–2) and $(CA)_xRY$ (where in a mixture of primers, R is a purine of approximately half in amount as adenine, and approximately half in amount as guanine; where in a mixture of primers Y is a pyrimidine of approximately half in amount as cytosine, and approximately half in amount as thymine; and wherein x is a number from about 6 to 16, with a preferred number of 8) (representative examples of these primers are shown as SEQ ID NOs:3–8) were synthesized and endlabeled with a detectable label comprising $\gamma$-$^{32}$P-ATP by using T4 polynucleotide kinase. In another variation of this embodiment, it was found that other $(CA)_x$ primers may be used: $(CA)_xRR$ where R is a purine selected from the group consisting of adenine, guanine, and a combination thereof (in a mixture of primers), and wherein x is a number from about 6 to 16, with a preferred number of 8 (representative examples of these primers are shown as SEQ ID NOs:28–29); and $(CA)_xYY$ wherein Y is a pyrimidine selected from the group consisting of cytosine, thymine, and uracil, and wherein x is a number from about 6 to 16, with a preferred number of 8) (representative examples of these primers are shown as SEQ ID NOs:30–38).

DNA was prepared from tissue samples (either tumor or normal mucosa) from patients with sporadic colorectal cancer. Small pieces of tumor were digested with 1 μg/ml proteinase K for 3 hours at 65° C., followed by 0.5 μg/ml RNase treatment for 1 hour, and then further purified by extraction and precipitation. In a 20 μl reaction volume, 50 ng of genomic DNA and 0.3 units of thermostable DNA polymerase are added to amplification buffer (10 mM Tris-HCl, pH 9.0, 2% formamide, 50 mM KCl, 0.2 mM dNTPs, 1.5 mM MgCl$_2$, 0.01% gelatin, 0.01% detergent). After an initial denaturation for 3 minutes at 94° C., the amplification was cycled thirty times at 30 seconds at 94° C., 45 seconds at 52° C., and 2 minutes at 72° C., followed by a final 7 minute extension at 72° C. Five microliters of each amplification reaction were analyzed on a nondenaturing 8% polyacrylamide gel without urea, buffered with electrophoresis buffer (0.89 mM Tris-borate, pH 8.3, 2 mM EDTA). Electrophoresis was performed at 80 watts for 22 minutes, followed by 50 watts for 3400 volt-hours. The gels were dried and placed on x-ray film for autoradiographic exposure. Alterations (changes in banding pattern) may be visually viewed, or scanned and detected by other means (dependent upon the nature of the label molecule used) including, but not limited to, densitometry or fluorimetry. Tumor-specific alterations were detected as gains, losses, and intensity changes in the pattern of amplified bands. In developing the method, the assay was repeated 6 times for each comparison sample pair (tumor sample and normal sample) to ensure reproducibility. Tumor-specific alterations that recurred in at least 4 of the 6 assays were counted in the determination of the instability index for each tumor sample. In the method of the present invention, the majority of the alterations due to genomic instability that were observed in each tumor sample were present in at least 5 of the 6 assays performed.

To clone and sequence the altered bands detected in the method of the present invention, the 3'-based primer was modified by the addition of nucleotides containing a restriction site (e.g., 8 nucleotides containing an EcoR I site). Amplified products are then resolved by gel electrophoresis. The altered product of interest is cut out from the gel, eluted, and reamplified. Reamplified product is digested with the restriction enzyme, and then ligated as an insert into a vector. The insert may then be sequenced.

EXAMPLE 2

Using the techniques according to Example 1, and using either the 3'-anchored $(CA)_8RG$ (representative examples of these primers are shown as SEQ ID NOs:1–2) or $(CA)_8RY$ primers (representative examples of these primers are shown as SEQ ID NOs:3–8), amplified products from 59 comparison sample pairs were examined. Each of $(CA)_8RG$ or $(CA)_8RY$ primers (differing only by the 3'anchor sequence) generated a unique set of approximately 40 bands of amplified products which were resolved by gel electrophoresis. By including normal mucosa, mucosa found proximal or distal to the tumor, in the comparison sample pair in the method according to the present invention, it was confirmed that the alterations observed in the tumor samples were tumor-specific and not the result of possible genomic variation in different regions of the tissue (e.g., colon). Also, the samples were analyzed for microsatellite instability using a method described previously (Petersen et al., 1991, *Genetics* 87:401–404; Linblom et al., 1993, *Nature Genet.* 5:279–282; Peltomaki et al., 1993, *Science* 260:810–812). Table 1 is an assessment of the 59 tumors for microsatellite instability (replicative error phenomenon (RER) and loss of heterozygosity (LOH)) compared to the assessment of the same tumors for genomic instability using a method according to the present invention. As illustrated in Table 1, greater than 80% of all tumors assayed according to a method of the present invention showed at least one altered band, and alterations in more than 10% of the bands in the banding pattern, as compared to normal, were observed in 4 tumors.

TABLE 1

Genomic Instability and Clinical Features

| Pt. No. | Size (cm) | Stage | Site | DFS (months) | Surv. (months) | RER | LOH | GEN INSTA |
|---|---|---|---|---|---|---|---|---|
| 3039 | 3.5 | 3 | LC | 6 | 1.6 | + | − | 0 |
| 3116 | 2.8 | 2 | R | NFA | NFA | − | − | 0 |
| 3120 | 5 | 1 | R | 40 | 40 | + | − | 0 |
| 3127 | 6 | 2 | RC | 32 | 32 | − | + | 0 |
| 3131 | 2.5 | 1 | R | 35 | 35 | − | − | 0 |
| 3201 | 4.1 | 1 | R | 18 | 18 | − | − | 0 |
| 3205 | 3.6 | 1 | RC | 19 | 19 | − | − | 0 |
| 3209 | 3 | 3 | LC | 18 | 18 | − | − | 0 |
| 6380 | 3.5 | 3 | R | 12 | 12 | − | − | 0 |
| 6392 | 8.5 | 4 | RC | — | 6 | − | − | 0 |
| 3025 | 1.7 | 4 | R | — | 15 | − | − | 1.3 |
| 3141 | 10 | 4 | RC | — | 22 | − | − | 1.3 |
| 3147 | 6.5 | 4 | RC | — | 10 | − | + | 1.3 |
| 3151 | 6.5 | 2 | RC | 28 | 28 | − | − | 1.3 |
| 3184 | 5.2 | 1 | R | 23 | 23 | − | + | 1.3 |
| 3203 | NA | 4 | RC | — | 3 | − | − | 1.3 |
| 3207 | 4 | 4 | LC | — | 18 | − | − | 1.3 |
| 3215 | 6 | 4 | R | — | 15 | − | − | 1.3 |
| 6378 | 1.4 | 1 | R | 10 | 10 | − | − | 1.3 |
| 6384 | 5 | 3 | R | 3 | 4 | − | − | 1.3 |
| 3027 | NA | 1 | RC | 37 | 37 | − | − | 2.6 |
| 3041 | 1.5 | 1 | LC | 13 | 20 | − | − | 2.6 |
| 3043 | 6.5 | 3 | LC | 18 | 18 | − | − | 2.6 |
| 3122 | 10 | 2 | RC | 39 | 39 | + | − | 2.6 |
| 3155 | 3.5 | 2 | R | 24 | 24 | − | − | 2.6 |
| 3195 | 2.5 | 3 | LC | 23 | 23 | − | − | 2.6 |
| 3929 | 4 | 1 | R | 14 | 14 | − | − | 2.6 |
| 6368 | 5 | 3 | R | 20 | 20 | − | − | 2.6 |
| 6372 | 3 | 2 | RC | 15 | 15 | + | − | 2.6 |
| 6388 | 5.5 | 2 | R | 6 | 6 | − | − | 2.6 |
| 3029 | 5.5 | 3 | LC | 8 | 19 | − | − | 3.9 |
| 3031 | 6 | 1 | R | 27 | 27 | − | − | 3.9 |
| 3118 | 3 | 1 | RC | 39 | 39 | − | − | 3.9 |
| 3157 | 5.5 | 1 | R | 27 | 27 | − | − | 3.9 |
| 3187 | 8 | 3 | R | 18 | 18 | − | − | 3.9 |
| 3211 | 4.5 | 1 | R | 16 | 16 | − | − | 3.9 |
| 6374 | 5 | 2 | RC | 17 | 17 | − | + | 3.9 |
| 6376 | 4 | 1 | R | 13 | 13 | − | − | 3.9 |
| 6382 | NA | 4 | R | — | 3 | − | − | 3.9 |
| 3021 | 3 | 1 | LC | 35 | 35 | − | − | 5.2 |
| 3137 | 3 | 0 | RC | 34 | 34 | − | − | 5.2 |
| 3145 | 5 | 1 | RC | 24 | 24 | − | − | 5.2 |
| 3182 | 4 | 3 | R | 21 | 25 | − | + | 5.2 |
| 6386 | 5 | 4 | RC | — | 8 | − | − | 5.2 |
| 3035 | 4.5 | 4 | R | NFA | NFA | − | − | 6.5 |
| 3125 | 2.5 | 4 | LC | — | 11 | − | + | 6.5 |
| 3199 | 4.5 | 2 | R | 14 | 14 | − | − | 6.5 |
| 3936 | NA | 2 | R | 12 | 12 | − | − | 6.5 |
| 6394 | 3.3 | 2 | R | 7 | 8 | − | − | 6.5 |
| 3023 | 10 | 1 | RC | 35 | 35 | − | + | 7.8 |
| 3149 | 5 | 4 | LC | — | 28 | − | + | 7.8 |
| 3213 | 7.5 | 3 | R | 17 | 17 | − | − | 7.8 |
| 6370 | 2 | 3 | RC | 22 | 22 | − | − | 7.8 |
| 3177 | 3.2 | 4 | RC | — | 8 | − | − | 9.1 |
| 3033 | 4 | 4 | RC | — | 30 | − | + | 10.4 |
| 3153 | 3 | 3 | R | 9 | 14 | + | + | 10.4 |
| 3135 | 1.8 | 1 | RC | 26 | 26 | + | − | 11.7 |

TABLE 1-continued

Genomic Instability and Clinical Features

| Pt. No. | Size (cm) | Stage | Site | DFS (months) | Surv. (months) | RER | LOH | GEN INSTA |
|---|---|---|---|---|---|---|---|---|
| 3143 | 0.3 | 3 | R | NFA | NFA | – | – | 11.7 |
| 3180 | 4 | 2 | RC | 40 | 40 | – | + | 13 |

Figure 4:
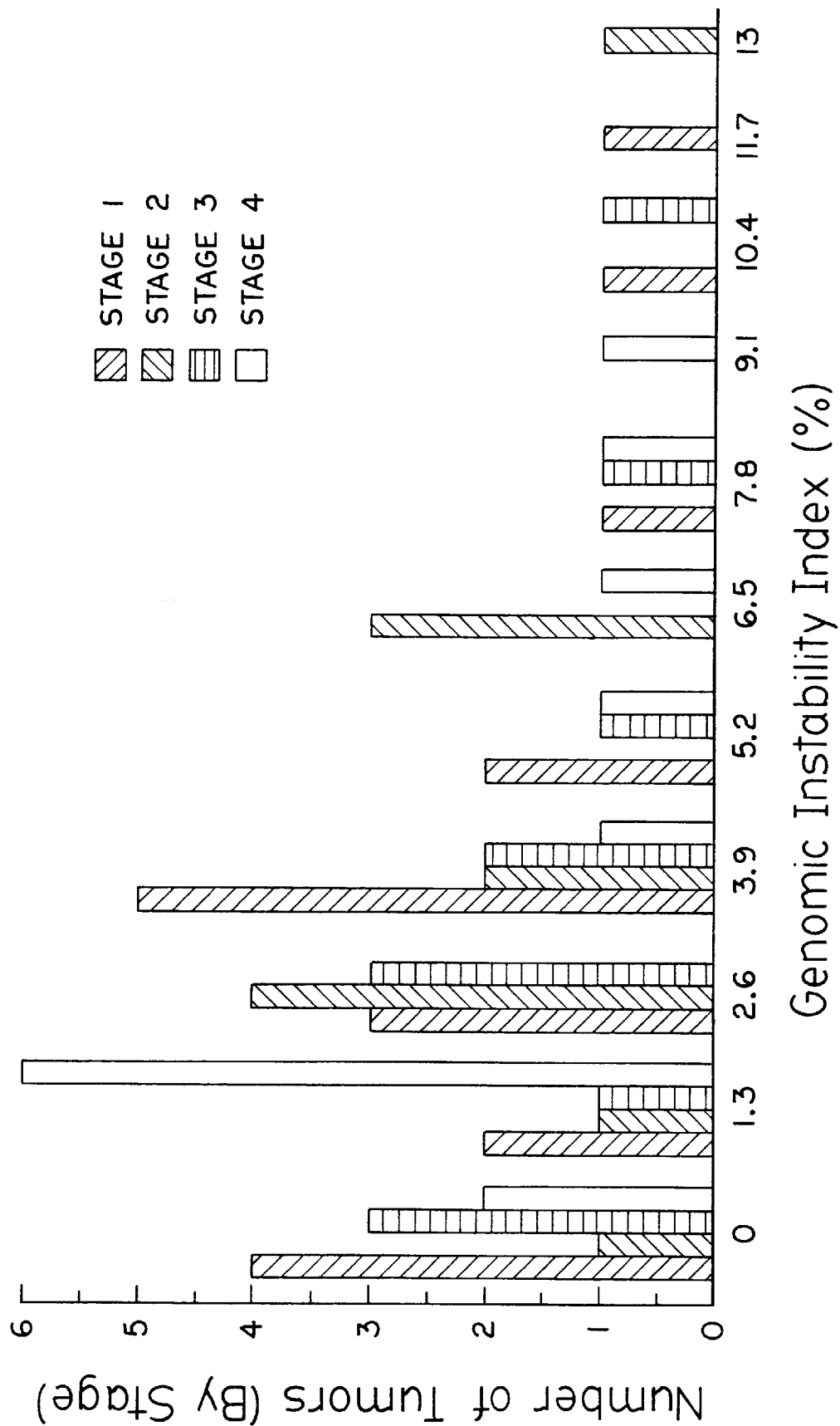
FIG. 4 is a histogram illustrating the range of genomic instability as related to tumor stage.

DFS = disease-free survival; SURV = overall survival; RER = presence of replicative error phenomenon (microsatellite instability) at ≧2 loci out of 5 examined; LOH = presence of loss of heterozygosity (microsatellite instability) at ≧1 locus out of 5; GEN INSTA = genomic instability index (%) as detected by inter-SSR PCR; LC = left colon; R = rectum; RC = right colon; NA = not available; NFA = no follow-up available Using a method according to the present invention, the medium genomic instability index for all 59 tumors was 3.3%; that is, 3.3% of all bands generated for normal colonic mucosa were altered in colonic tumor DNA. Although the number of genomic lesions might be expected to be greater in tumors of a higher stage if such lesions occurred stochastically during tumor progression, the actual index of genomic instability was found to vary independently of tumor stage at diagnosis (see FIG. 4). In all cases evaluated to date using a method according to the present invention, adenomatous polyps have demonstrated genomic instability indices above the median, including one polyp (index value= 3.9%) in a patient with a synchronous carcinoma. In this particular patient, 3 out of 7 bands altered in the primary tumor were also altered in the adenoma. Together, these data suggest that initiations of genomic instability can occur at an early stage of tumor development. It was also interesting to note that of four patients whom were followed and whom had a genomic instability index greater than 10, two had recurrences within 2 years after surgery. Thus, the genomic instability index may provide clinically significant indices.

Figure 5:
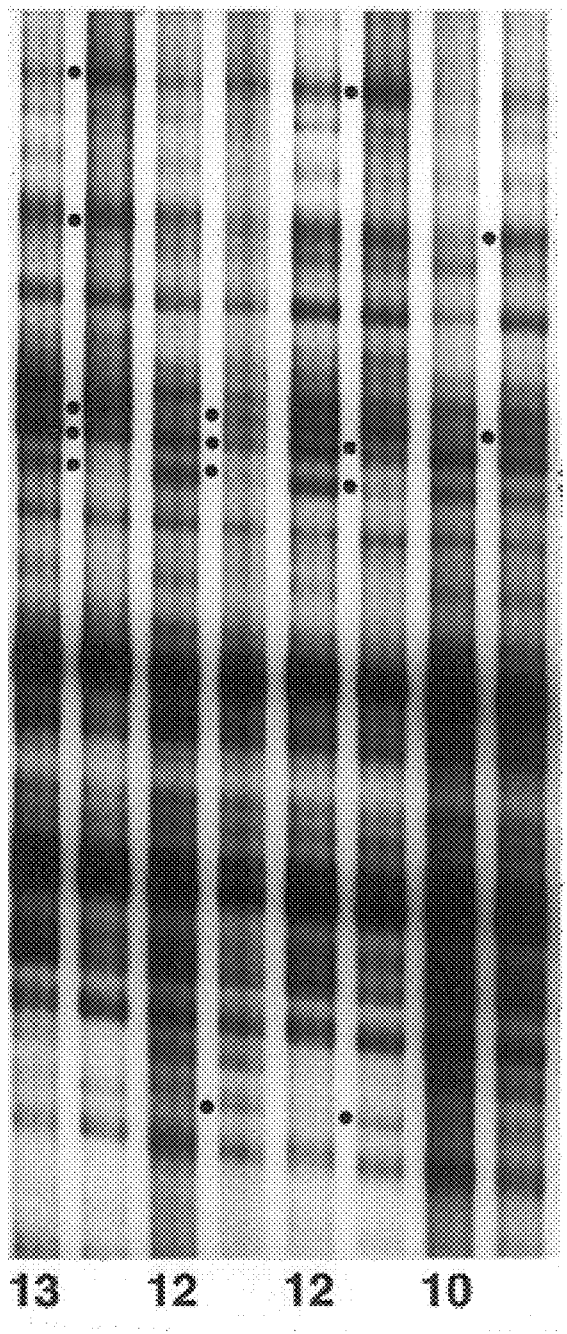
FIG. 5 is an illustration of a comparison of band alterations from several highly genomically unstable tumors, detected using a method according to the present invention.

To determine whether any of the band alterations were shared between the colonic tumors, altered bands were compared in the most unstable tumors. This comparison, illustrated in FIG. 5, shows that several electrophoretically identical bands were found to be altered frequently in the colonic tumors from different patients. These results suggest that the altered bands correspond to regions of the genome that are critical to tumor progression and/or these regions are preferentially altered by the mechanism(s) underlying genomic instability. In an attempt to distinguish between these two possibilities, several of these frequently altered bands were cloned and sequenced from a tumor (from patient no. 3180). DNA fragments contained CA repeats at both ends and ranged in size from 178 to 559 base pairs. One clone was homologous to a region in chromosome 16, neighboring a region which is often deleted in breast and prostate cancers, and is thought to be the site of an unknown tumor suppressor gene (see, e.g., Cleton-Jansen et al., 1994, *Genes, Chromosomes and Cancer* 9:101–107). Thus, cloning and sequencing of the altered bands can be used for the identification and mapping of altered regions/genes of the genome in diseased tissues. Further, precise definition of the kind of mutations detected may further yield important clues to novel mutator phenotypes that are active in one or more tumor types.

Figure 6:
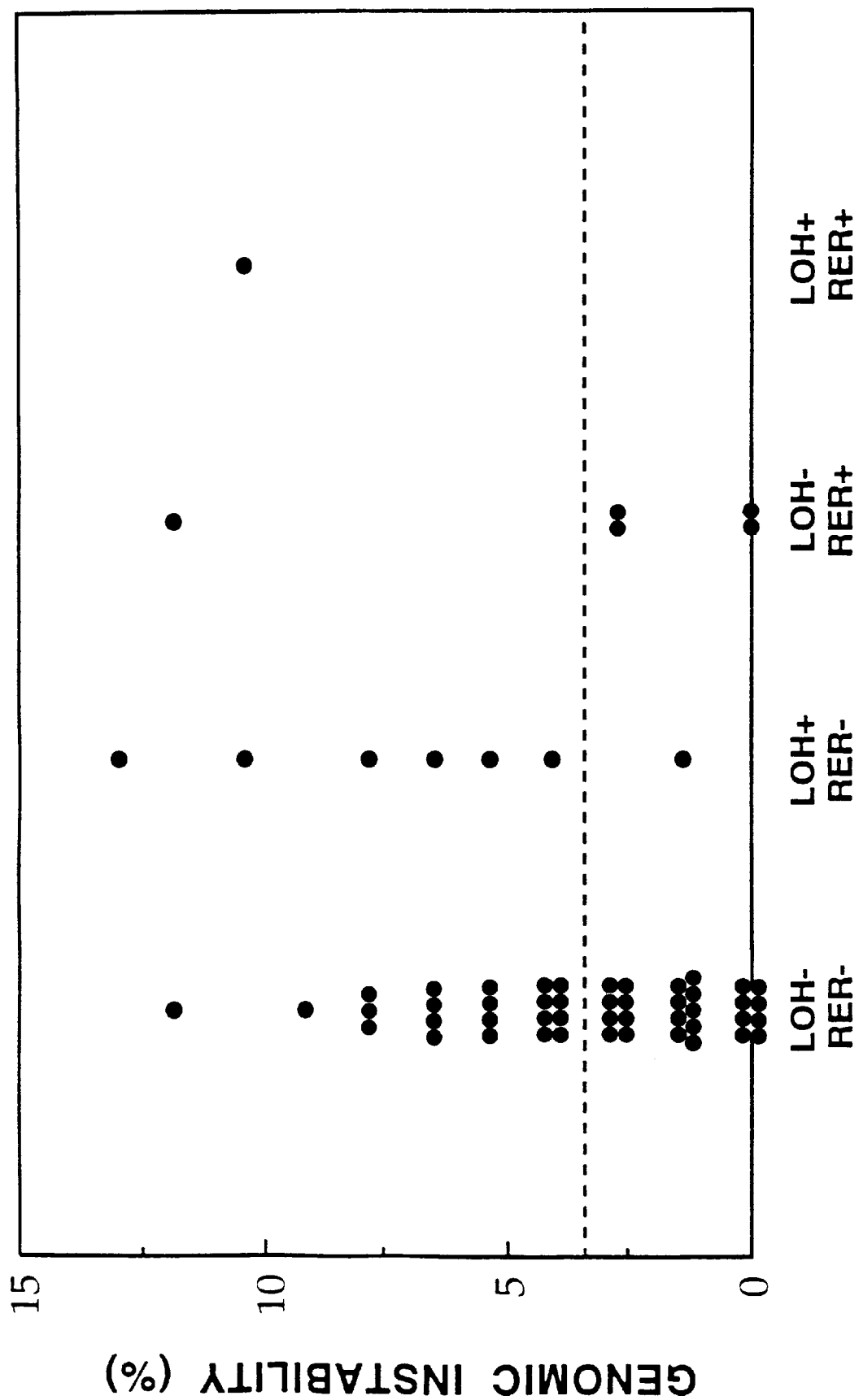
FIG. 6 is a graphic illustration of a comparison between a method according to the present invention for assessing genomic instability, and by a method for assessing microsatellite instability.

In analyzing these 59 tumors for microsatellite instability, 10% (6 tumors) were RER+, and 14% (8 tumors) were LOH+, with the remaining 45 tumors neither RER+ or LOH+. As illustrated in FIG. 6, the mean genomic instability index (determined according to a method of the present invention) in these 3 groups of tumors were 4.6%, 7.3%, and 3.3%, respectively.

EXAMPLE 3

The present invention is directed to the development of methods to assess genomic instability other than that which arises from defects in DNA mismatch repair (microsatellite instability). Such genomic instability appears to initiate the multistep process of carcinogenesis through alterations that include translocations, insertions, deletions, and gene amplification. One specific alteration is the mutation of genes suspected of playing a role in the development of cancer, including mutations in the p53 gene, the ras protooncogene, topoisomerase genes, and other tumor suppressor genes. For example, mutation of p53 is one of the most frequently encountered genetic alterations in solid tumors (Greenblatt et al., 1994, *Cancer Res.* 54:4855–4878). It is believed that the onset of genomic instability is an early event facilitating the several mutations required to effect carcinogenesis (Shibata et al., 1994, *Nature Genet.* 6:273–281). In contrast, it is believed that most often, p53 mutation is a late event, such as in the progression from adenoma to adenocarcinoma (Fearon et al., 1990, *Cell* 61:759–767). Is there a correlation between genomic instability as detected by the method comprising the first embodiment of the present invention; i.e., is there a greater incidence of p53 mutations in tumors that show increased genomic instability? Alternately, is there a negative correlation between the incidence of p53 mutations and genomic instability, suggesting a separate pathway, as for example, in the sporadic carcinogenesis of highly genomically unstable tumors?

Using the techniques according to Examples 1 and 2, and using either the 3'-anchored $(CA)_8RG$ (representative examples of these primers are shown as SEQ ID NOs:1–2) or 3'-anchored $(CA)_8RY$ primers (representative examples of these primers are shown as SEQ ID NOs:3–8), amplified products from 58 sporadic colorectal tumors were examined and compared to analysis of p53 mutations of the same tumors. p53 mutations were analyzed by using commercially available primers (Clontech) homologous to the 5' and 3' ends of each of exons 5 through 9 using single strand conformational polymorphism (SSCP)-PCR according to methods known in the art (Greenblatt et al., 1994, supra). The relationship between the incidence of p53 mutations, as measured by (SSCP)PCR, and the degree of genomic instability, as measured by amplification using the 3'-anchored $(CA)_8RG$ or 3'-anchored $(CA)_8RY$ primers, was assessed by statistical analysis (Chi-squared analysis). The Student's t-test was performed to determine if there was any significant difference in the mean value of the genomic instability index for tumors with p53 mutations, and those having a wild-type p53.

Of the 58 sporadic colorectal tumor specimens analyzed, 29 tumors contained p53 mutations, a frequency (50%) consistent with other published observations (Greenblatt et al., 1994, supra). As shown in Table 2, the mutations were distributed among exons 5–9 in the following manner: eight mutations in exon 5; nine mutations in exon 6; three mutations in exon 7; five mutations in exon 8; and eleven mutations in exon 9. It is noted that p53 mutations were identified in more than one exon in six of the 29 tumors. The median genomic instability index for the 29 tumors containing p53 mutations was 2.6%; whereas the median genomic instability index for the 29 tumors with wild type p53 (between exons 5–9) was 3.9%. Further, of the 29 tumors containing p53 mutations, 19 (65.5%) had an genomic instability index less than the combined median index of 3.3%. This is compared to 11 (37.9%) of 29 tumors containing wild type p53 having a genomic instability index of less than 3.3%. The mean genomic instability scores for the sets of tumors with p53 mutation and wild type p53 were 3.5% and 4.2%, respectively, with variances of 12.44 and 10.8, respectively. A Student's t-test was performed with p=0.44, suggesting no significant difference in the average genomic instability index value between these two groups. These analyses show that tumors with no or minimal evidence of genomic instability are more likely to harbor p53 mutations; i.e., the data shows that there is a significant negative association between the incidence of p53 mutation and the degree of overall genomic instability as measured by amplification using the 3'-anchored $(CA)_8RG$ or 3'-anchored $(CA)_8RY$ primers.

TABLE 2

Genomic Instability and p53 Status

| p53 Mutation | | | p53 wild type | |
| --- | --- | --- | --- | --- |
| Patient number | genomic instability index % | Exon | Patient number | genomic instability index % |
| 3039 | 0 | 9 | 3131 | 0 |
| 3116 | 0 | 6, 9 | 3201 | 0 |
| 3120 | 0 | 5 | 3205 | 0 |
| 3127 | 0 | 5, 6 | 3209 | 0 |
| 6392 | 0 | 6 | 6380 | 0 |
| 3025 | 1.3 | 8, 9 | 3141 | 1.3 |
| 3147 | 1.3 | 6 | 3207 | 2.6 |
| 3151 | 1.3 | 8 | 3215 | 1.3 |
| 3184 | 1.3 | 6 | 3027 | 2.6 |
| 3203 | 1.3 | 5 | 3122 | 2.6 |
| 6378 | 1.3 | 7, 9 | 3195 | 2.6 |
| 6384 | 1.3 | 6, 9 | 3031 | 3.9 |
| 3041 | 2.6 | 9 | 3118 | 3.9 |
| 3043 | 2.6 | 6 | 3157 | 3.9 |
| 3155 | 2.6 | 6 | 3187 | 3.9 |
| 3929 | 2.6 | 9 | 3211 | 3.9 |
| 6368 | 2.6 | 5 | 6374 | 3.9 |
| 6372 | 2.6 | 9 | 6376 | 3.9 |
| 6388 | 2.6 | 8 | 3137 | 5.2 |
| 3029 | 3.9 | 9 | 3145 | 5.2 |
| 6382 | 3.9 | 6, 8 | 3182 | 5.2 |
| 3021 | 5.2 | 9 | 3035 | 6.5 |
| 6386 | 5.2 | 9 | 3936 | 6.5 |
| 3125 | 6.5 | 5 | 6394 | 6.5 |
| 3199 | 6.5 | 5 | 3023 | 7.8 |
| 3213 | 7.8 | 7 | 3149 | 7.8 |
| 3033 | 10.4 | 5 | 3177 | 9.1 |
| 3143 | 11.7 | 7 | 3153 | 10.4 |
| 3180 | 13 | 6 | 3135 | 11.7 |

EXAMPLE 4

A second embodiment of the present invention was developed to detect genomic instability not detected by the use of 3'-anchored $(CA)_x$ primers in amplification of genomic DNA from tumors. This second embodiment comprises a method for assessing genomic instability, while allowing for simultaneously assessing the overall frequency of methylation alterations, using 3'-anchored $(CG)_xRG$ primers (representative examples of these primers are shown as SEQ ID NOs:9–10), 3'-anchored $(CG)_xRY$ primers (representative examples of these primers are shown as SEQ ID NOs:11–16), 3'-anchored $(CG)_xRR$ primers (representative examples of these primers are shown as SEQ ID NOs:17–18), or 3'-anchored $(CG)_xYY$ primers (representative examples of these primers are shown as SEQ ID NOs:19–27) in the amplification process. Unexpectedly, these $(CG)_x$-based primers are significantly more sensitive in scanning the genome for genomic instability by amplifying sequences predominantly in close proximity to genes. Amplifying CpG islands, and the sequences between the islands, results in detection of sequences which may show alteration in methylation patterns, and/or mutation such as by chemical modification. Sequences between the islands can be optimally amplified if (i) the CG repeats are within about 2 kb of each other, and (ii) their orientation is tail to tail.

In illustrating this method according to this second embodiment, 3'-anchored primers were synthesized: $(CG)_xRG$, wherein R is a purine selected from the group consisting of adenine and guanine, and wherein x is a number from about 3 to 7, with a preferred number of about 4 to 5 (representative examples of these primers are shown as SEQ ID NOs:9–10); and $(CG)_xRY$, wherein R is a R is a purine selected from the group consisting of adenine and guanine, Y is a pyrimidine selected from the group consisting of cytosine, thymine, and uracil, and wherein x is a number from about 3 to 7, with a preferred number of about 4 to 5 (representative examples of these primers are shown as SEQ ID NOs:11–16). The RG or RY portion at the 3' end of the (CG)-based primers anchors the primer to sequences outside the CpG islands. Enzymatically amplifying DNA sequences, for example by using the inter-SSR PCR method according to Example 1 except that 3'-anchored $(CG)_xRG$ or 3'-anchored $(CG)_xRY$ primers were used in the amplification process, can result in amplified products from genomic DNA.

Figure 7:
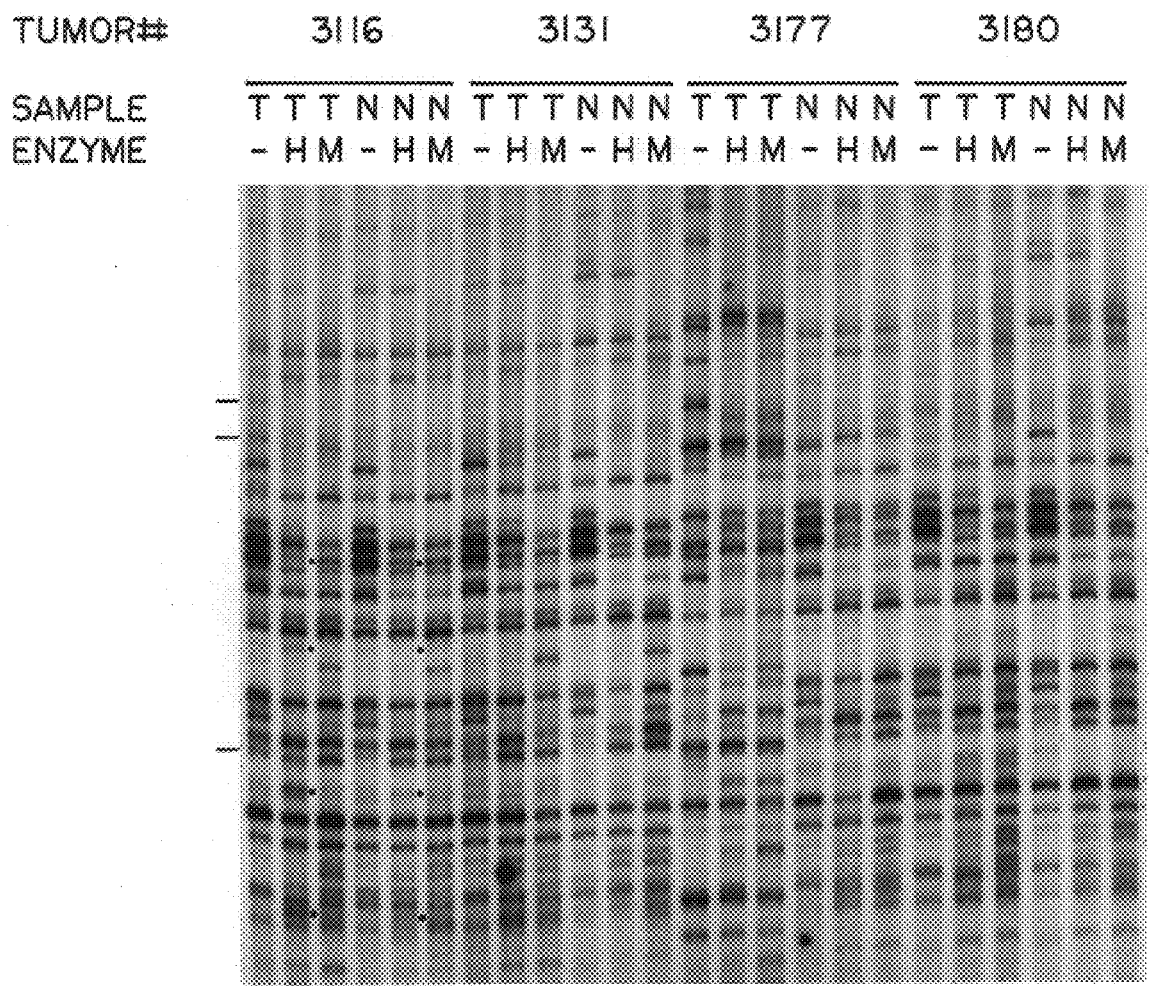
FIG. 7 is an illustration of comparisons of band alterations from several genomically unstable tumors, and of alterations in methylation detected using a method according to the present invention.

In a particular illustration of this second embodiment, $(CG)_4RY$ primers (representative examples of these primers are shown as SEQ ID NOs:11–16) were used to generate amplified products from 20 comparison sample pairs. As illustrated by FIG. 7 for four comparison sample pairs (3116, 3131, 3177, and 3180), the $(CG)_4RY$ primers generated a unique set of approximately 40 bands of amplified products which were resolved by gel electrophoresis. Tumor-specific alterations were detected (via, e.g., detectable label) as gains, losses, and intensity changes in the pattern of amplified bands as compared to normal mucosa.

Figure 8:
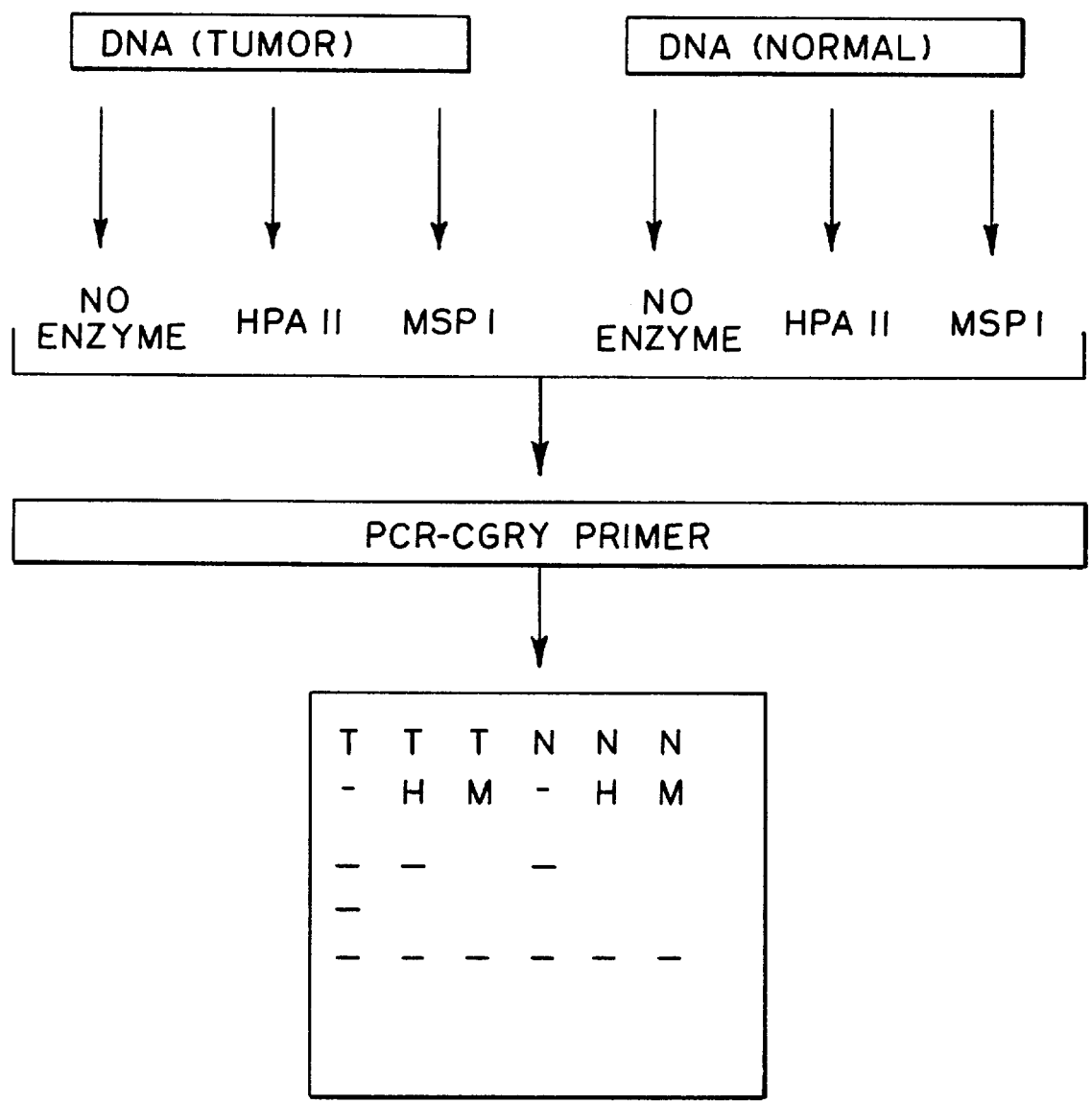
FIG. 8 is a schematic of the methylation fingerprinting process according to the present invention.

The DNA molecules in the comparison sample pair may be subjected to analysis by a reagent that detects methylation status. These reagents include, but are not limited to, restriction enzymes. As an illustration of methylation fingerprinting using the method according to the present invention, two restriction enzymes were added to the genomic DNA prior to enzymatic amplification using the $(CG)_4RY$ primers. Both the tumor-derived DNA and the DNA derived from the normal mucosa from the same individual were restricted in separate reactions with two isoschizomers Hpa II and Msp I using temperatures and buffers according to the manufacturer's instructions. While the recognition site is the same for each enzyme, Hpa II will cut the recognition site only if the second cytosine of the site is unmethylated. In contrast, Msp I will cut regardless of methylation status. After restriction, the DNAs are amplified and resolved, for example, on polyacrylamide nondenaturing gels. FIG. 8 is a schematic of the methylation fingerprinting process according to the present invention using restriction enzymes, wherein Hpa II digested DNA ("H") and Msp I digested DNA ("M") are compared. Other restriction enzyme pairs useful in the methylation fingerprinting process according to the present invention include, but are not limited to, SmaI and Xma I; Eco RII and Bst NI; Acc III and Bsp MII; Mbo I and Sau 3AI; Mbo I and Dpn I; and Mfi I and Xho II.

Differences in methylation can be assessed by band by band comparison of amplified products containing detectable label. Changes in overall methylation status are observed as differences between Hpa II-digested tumor DNA and Hpa II-digested normal mucosa DNA with absence of the same band in Msp I-digested tumor and Msp I-digested normal mucosa DNA. Presence of such a band in one or the other Msp I-digested DNA samples is indicative of gains or losses of the restriction site as affected by methylation pattern. Thus, DNA can be assessed for genomic instability, while simultaneously assessed for methylation fingerprinting, as illustrated in FIG. 7 for patient no. 3116. Using a method according to the second embodiment of the present invention, tumor-specific DNA strand break-initiated alterations which were detected in the tumor DNA from patient no. 3116 are denoted by "—" at the left of lane 1; whereas alterations in methylation pattern of the tumor DNA from patient no. 3116 are indicated by (●). As shown, the lower three bands in the comparison pairs of Hpa II-digested DNA are accompanied by loss of the band following Msp I digestion. This result indicates that hypermethylation events have occurred specifically in the tumor at all three of these regions containing the restriction site. As determined from the banding pattern of amplified DNA, a methylation index can be calculated as: (number of bands representing altered methylation/total number of normal bands)×100.

In practicing the method of the present invention to assess genomic instability, the method utilizing the 3'-anchored $(CA)_xRG$, 3'-anchored $(CA)_xRY$, 3'-anchored $(CA)_xRR$, or 3'-anchored $(CA)_xYY$ primers (first embodiment), or the method utilizing the 3'-anchored $(CG)_xRG$, 3'-anchored $(CG)_xRY$, 3'-anchored $(CG)_xRR$, or 3'-anchored $(CG)_xYY$ primers (second embodiment), or a combination of primers from both embodiments of the method, may be employed. Additionally, the methylation fingerprinting process, as illustrated herein, may be used in conjunction with the method utilizing the 3'-anchored $(CA)_x$ primers according to the first embodiment, or the method utilizing the 3'-anchored $(CG)_x$ primers according to the second embodiment, or a combination of these two methods. The resultant data thus provides quantitation of both overall methylation status and overall genomic instability for use as clinical indices. In the method according to the present invention for quantitating genomic instability, it may be desirable to have in assay kit form components selected from the group consisting of 3'anchored primers $((CA)_xRG, (CA)_xRY, (CA)_xRR, (CA)_xYY, (CG)_xRG, (CG)_xRY, (CG)_xRR,$ or $(CG)_xYY$ primers, or a combination thereof), a detectable label and reagents for incorporating the label directly or indirectly into the primers, enzyme and buffer required for the amplification reaction, and reagents for detecting methylation status (e.g., restriction enzymes and respective reaction buffer(s)), and various combinations thereof.

The foregoing description of the specific embodiments of the present invention have been described in detail for purposes of illustration. In view of the descriptions and illustrations, others skilled in the art can, by applying, current knowledge, readily modify and/or adapt the present invention for various applications without departing from the basic concept, and therefore such modifications and/or adaptations are intended to be within the meaning and scope of the appended claims.

We claim:

1. A method for detecting genomic instability, independent of microsatellite alterations, comprising the steps of:
   (a) treating, in a separate reaction, DNA isolated from tumor cells, and DNA isolated from normal cells of the same individual as the tumor cells, with oligonucleotide primers under conditions promoting hybridization, wherein the oligonucleotide primers are selected from the group consisting of
      (i) a nucleotide sequence $(CG)_x RG$, wherein R is a purine selected from the group consisting of adenine and guanine, and wherein x is a number from about 3 to 7,
      (ii) a nucleotide sequence $(CG)_x RY$ wherein R is a purine selected from the group consisting of adenine and guanine, wherein Y is a pyrimidine selected from the group consisting of cytosine, thymine, and uracil, and wherein x is a number from about 3 to 7,
      (iii) a nucleotide sequence $(CG)_x RR$, wherein R is a purine selected from the group consisting of adenine, guanine, and wherein x is a number from about 3 to 7,
      (iv) a nucleotide sequence $(CG)_x YY$, wherein Y is a pyrimidine selected from the group consisting of cytosine, thymine, and uracil, and wherein x is a number from about 3 to 7,
      (v) a nucleotide sequence $(CA)_x RG$ wherein R is a purine selected from the group consisting of adenine and guanine, and wherein x is a number from about 6 to 16,
      (vi) a nucleotide sequence $(CA)_x RY$ wherein R is a purine selected from the group consisting of adenine and guanine, wherein Y is a pyrimidine selected from the group consisting of cytosine, thymine and uracil, and wherein x is a number from about 6 to 16, (vii) a nucleotide sequence $(CA)_x RR$ wherein R is a purine selected from the group consisting of adenine and guanine, and wherein x is a number from about 6 to 16, (viii) a nucleotide sequence $(CA)_x YY$ wherein Y is a pyrimidine selected from the group consisting of cytosine, thymine and uracil, and wherein x is a number from about 6 to 16, and (ix) a combination of the primers of (i), (ii), (iii), (iv), (v), (vi), (vii), and (viii);

(b) amplifying the DNA molecules using the oligonucleotide primers as a point of initiation for DNA strand synthesis;

(c) resolving the amplified products, from the amplification of tumor cell DNA and from the amplification of normal cell DNA, into a pattern of amplified bands; and (d) comparing the pattern of bands from the amplified tumor cell DNA to the pattern of bands from the amplified normal cell DNA and detecting one or more alterations in the pattern from the amplified tumor cell DNA as compared to the pattern from the amplified normal cell DNA, wherein the one or more alterations are selected from the group consisting of gains, losses, intensity changes, and a combination thereof, and wherein the detection of one or more alterations is indicative of the genomic instability.

2. The method for detecting genomic instability according to claim 1, wherein in a combination of primers the R of the oligonucleotide primers is a purine of approximately half in amount as adenine and approximately half in amount as guanine.

3. The method for detecting genomic instability according to claim 1, wherein in a combination of primers the Y of the oligonucleotide primers is a pyrimidine of approximately half in amount as cytosine and approximately half in amount as thymine.

4. The method for detecting genomic instability according to claim 1, wherein the oligonucleotide primers are selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, a nucleotide sequence which differs from SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38 by one base change or substitution therein, and a combination thereof.

5. The method for detecting genomic instability according to claim 1, wherein the oligonucleotide primers further comprise a detectable label bound to the primers.

6. The method according to claim 1, further comprising determining from the banding patterns of amplified DNA, a genomic instability index calculated by a formula:

(number of alterations in the banding pattern from the amplified tumor cell DNA/total number of bands in the pattern from the amplified normal cell DNA)×100.

7. The method for detecting genomic instability according to claim 1, wherein the method further comprises a process for assessing alterations in methylation between the tumor cell DNA as compared to the normal cell DNA, the process comprising subjecting the DNA isolated from tumor cells, and the DNA isolated from normal cells, prior to the amplification of step (b), to digestion in separate reactions with two isoschizomer restriction enzymes of a restriction enzyme pair, wherein a first restriction enzyme cuts only an unmethylated recognition site and a second restriction enzyme cuts regardless of methylation status; and after resolving the amplified products of step (c), comparing the pattern of bands from each of the amplified DNA resulting from the tumor cell DNA digested with the first restriction enzyme, the amplified DNA resulting from the tumor cell DNA digested with the second restriction enzyme, the amplified DNA resulting from the normal cell DNA digested with the first restriction enzyme, and the normal cell DNA digested with the second enzyme, wherein an alteration in methylation is indicated by detection of a difference in the banding pattern between amplified DNA resulting from tumor cell DNA digested with the first restriction enzyme compared to the banding pattern of amplified DNA resulting from the normal cell DNA digested with the first restriction enzyme, and a difference in the banding pattern between amplified DNA resulting from the tumor cell DNA digested with the first restriction enzyme compared to the banding pattern of amplified DNA resulting from the tumor cell DNA digested with the second restriction enzyme.

8. The method according to claim 7, wherein the first restriction enzyme is Hpa II, and the second restriction enzyme is Msp I.

9. The method according to claim 7, wherein the restriction enzyme pair is selected from the pairs consisting of SmaI and Xma I, Eco RII and Bst NI, Acc III and Bsp MII, Mbo I and Sau 3AI, Mbo I and Dpn I, and Mfi I and Xho II.

10. The method according to claim 7, wherein in a combination of primers the R of the oligonucleotide primers is a purine of approximately half in amount as adenine and approximately half in amount as guanine.

11. The method according to claim 7, wherein in a combination of primers the Y of the oligonucleotide primers is a pyrimidine of approximately half in amount as cytosine and approximately half in amount as thymine.

12. The method according to claim 7, wherein the oligonucleotide primers are selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, a nucleotide sequence which differs from SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38 by one base change or substitution therein and a combination thereof.

13. The method according to claim 7, wherein the oligonucleotide primers further comprise a detectable label bound to the primers.

14. The method according to claim 7, further comprising determining from the banding patterns of amplified DNA, a methylation index calculated by a formula:

(number of bands representing altered methylation/total number of bands in the pattern from the amplified normal cell DNA)×100.

15. A method of detecting genomic instability, independent of microsatellite alterations, comprising using 3'-anchored oligonucleotide primers selected from the group consisting of $(CG)_x$-based primers, $(CA)_x$-based primers, or a combination thereof, to separately amplify DNA isolated from tumor cells and DNA isolated from normal cells from the same individual; electrophoretically separating the amplified nucleic acid products; and comparing the electrophoretically separated products amplified from tumor DNA to the electrophoretically separated products amplified from normal cell DNA to detect the genomic instability.

* * * * *

SEQUENCE LISTING (1) GENERAL INFORMATION:

(iii) NUMBER OF SEQUENCES: 38

(2) INFORMATION FOR SEQ ID NO:1 :

(i) SEQUENCE CHARACTERISTICS:
      (A) LENGTH:  18 nucleotides
      (B) TYPE: nucleic acid
      (C) STRANDEDNESS: single-stranded
      (D) TOPOLOGY: linear (ii) MOLECULE TYPE: DNA (iii) HYPOTHETICAL: No (iv) SEQUENCE DESCRIPTION: SEQ ID NO:1 :

CACACACACA CACACAAG                                      18

(2) INFORMATION FOR SEQ ID NO:2 :

(i) SEQUENCE CHARACTERISTICS:
      (A) LENGTH:  18 nucleotides
      (B) TYPE: nucleic acid
      (C) STRANDEDNESS: single-stranded
      (D) TOPOLOGY: linear (ii) MOLECULE TYPE: DNA (iii) HYPOTHETICAL: No (iv) SEQUENCE DESCRIPTION: SEQ ID NO:2 :

CACACACACA CACACAGG                                                       18

(2) INFORMATION FOR SEQ ID NO:3 :

(i) SEQUENCE CHARACTERISTICS:
        (A) LENGTH:  18 nucleotides
        (B) TYPE: nucleic acid
        (C) STRANDEDNESS: single-stranded
        (D) TOPOLOGY: linear (ii) MOLECULE TYPE: DNA (iii) HYPOTHETICAL: No (iv) SEQUENCE DESCRIPTION: SEQ ID NO:3 :

CACACACACA CACACAAC                                                       18

(2) INFORMATION FOR SEQ ID NO:4 :

(i) SEQUENCE CHARACTERISTICS:
        (A) LENGTH:  18 nucleotides
        (B) TYPE: nucleic acid
        (C) STRANDEDNESS: single-stranded
        (D) TOPOLOGY: linear (ii) MOLECULE TYPE: DNA (iii) HYPOTHETICAL: No (iv) SEQUENCE DESCRIPTION: SEQ ID NO:4 :

CACACACACA CACACAAT                                                       18

(2) INFORMATION FOR SEQ ID NO:5 :

(i) SEQUENCE CHARACTERISTICS:
        (A) LENGTH:  18 nucleotides
        (B) TYPE: nucleic acid
        (C) STRANDEDNESS: single-stranded
        (D) TOPOLOGY: linear (ii) MOLECULE TYPE: DNA (iii) HYPOTHETICAL: No (iv) SEQUENCE DESCRIPTION: SEQ ID NO:5 :

CACACACACA CACACAAU                                                       18

(2) INFORMATION FOR SEQ ID NO:6 :

(i) SEQUENCE CHARACTERISTICS:
        (A) LENGTH:  18 nucleotides
        (B) TYPE: nucleic acid
        (C) STRANDEDNESS: single-stranded
        (D) TOPOLOGY: linear (ii) MOLECULE TYPE: DNA (iii) HYPOTHETICAL: No (iv) SEQUENCE DESCRIPTION: SEQ ID NO:6 :

CACACACACA CACACAGC                                                       18

(2) INFORMATION FOR SEQ ID NO:7 :

(i) SEQUENCE CHARACTERISTICS:

(A) LENGTH: 18 nucleotides
        (B) TYPE: nucleic acid
        (C) STRANDEDNESS: single-stranded
        (D) TOPOLOGY: linear (ii) MOLECULE TYPE: DNA (iii) HYPOTHETICAL: No (iv) SEQUENCE DESCRIPTION: SEQ ID NO:7 :

CACACACACA CACACAGT                                                      18

(2) INFORMATION FOR SEQ ID NO:8 :

(i) SEQUENCE CHARACTERISTICS:
        (A) LENGTH: 18 nucleotides
        (B) TYPE: nucleic acid
        (C) STRANDEDNESS: single-stranded
        (D) TOPOLOGY: linear (ii) MOLECULE TYPE: DNA (iii) HYPOTHETICAL: No (iv) SEQUENCE DESCRIPTION: SEQ ID NO:8 :

CACACACACA CACACAGU                                                      18

(2) INFORMATION FOR SEQ ID NO:9 :

(i) SEQUENCE CHARACTERISTICS:
        (A) LENGTH: 10 nucleotides
        (B) TYPE: nucleic acid
        (C) STRANDEDNESS: single-stranded
        (D) TOPOLOGY: linear (ii) MOLECULE TYPE: DNA (iii) HYPOTHETICAL: No (iv) SEQUENCE DESCRIPTION: SEQ ID NO:9 :

CGCGCGCGAG                                                               10

(2) INFORMATION FOR SEQ ID NO:10 :

(i) SEQUENCE CHARACTERISTICS:
        (A) LENGTH: 10 nucleotides
        (B) TYPE: nucleic acid
        (C) STRANDEDNESS: single-stranded
        (D) TOPOLOGY: linear (ii) MOLECULE TYPE: DNA (iii) HYPOTHETICAL: No (iv) SEQUENCE DESCRIPTION: SEQ ID NO:10 :

CGCGCGCGGG                                                               10

(2) INFORMATION FOR SEQ ID NO:11 :

(i) SEQUENCE CHARACTERISTICS:
        (A) LENGTH: 10 nucleotides
        (B) TYPE: nucleic acid
        (C) STRANDEDNESS: single-stranded
        (D) TOPOLOGY: linear (ii) MOLECULE TYPE: DNA (iii) HYPOTHETICAL: No (iv) SEQUENCE DESCRIPTION: SEQ ID NO:11 :

CGCGCGCGAC                                                               10

(2) INFORMATION FOR SEQ ID NO:12 :

(i) SEQUENCE CHARACTERISTICS:
        (A) LENGTH: 10 nucleotides
        (B) TYPE: nucleic acid
        (C) STRANDEDNESS: single-stranded
        (D) TOPOLOGY: linear (ii) MOLECULE TYPE: DNA (iii) HYPOTHETICAL: No (iv) SEQUENCE DESCRIPTION: SEQ ID NO:12 :

CGCGCGCGAT                                                            10

(2) INFORMATION FOR SEQ ID NO:13 :

(i) SEQUENCE CHARACTERISTICS:
        (A) LENGTH: 10 nucleotides
        (B) TYPE: nucleic acid
        (C) STRANDEDNESS: single-stranded
        (D) TOPOLOGY: linear (ii) MOLECULE TYPE: DNA (iii) HYPOTHETICAL: No (iv) SEQUENCE DESCRIPTION: SEQ ID NO:13 :

CGCGCGCGAU                                                            10

(2) INFORMATION FOR SEQ ID NO:14 :

(i) SEQUENCE CHARACTERISTICS:
        (A) LENGTH: 10 nucleotides
        (B) TYPE: nucleic acid
        (C) STRANDEDNESS: single-stranded
        (D) TOPOLOGY: linear (ii) MOLECULE TYPE: DNA (iii) HYPOTHETICAL: No (iv) SEQUENCE DESCRIPTION: SEQ ID NO:14 :

CGCGCGCGGC                                                            10

(2) INFORMATION FOR SEQ ID NO:15 :

(i) SEQUENCE CHARACTERISTICS:
        (A) LENGTH: 10 nucleotides
        (B) TYPE: nucleic acid
        (C) STRANDEDNESS: single-stranded
        (D) TOPOLOGY: linear (ii) MOLECULE TYPE: DNA (iii) HYPOTHETICAL: No (iv) SEQUENCE DESCRIPTION: SEQ ID NO:15 :

CGCGCGCGGT                                                            10

(2) INFORMATION FOR SEQ ID NO:16 :

(i) SEQUENCE CHARACTERISTICS:
        (A) LENGTH: 10 nucleotides
        (B) TYPE: nucleic acid
        (C) STRANDEDNESS: single-stranded
        (D) TOPOLOGY: linear (ii) MOLECULE TYPE: DNA -continued

```
    (iii) HYPOTHETICAL: No (iv) SEQUENCE DESCRIPTION: SEQ ID NO:16 :

CGCGCGCGGU                                                              10

(2) INFORMATION FOR SEQ ID NO:17 :

(i) SEQUENCE CHARACTERISTICS:
        (A) LENGTH:  10 nucleotides
        (B) TYPE: nucleic acid
        (C) STRANDEDNESS: single-stranded
        (D) TOPOLOGY: linear (ii) MOLECULE TYPE: DNA (iii) HYPOTHETICAL: No (iv) SEQUENCE DESCRIPTION: SEQ ID NO:17 :

CGCGCGCGAA                                                              10

(2) INFORMATION FOR SEQ ID NO:18 :

(i) SEQUENCE CHARACTERISTICS:
        (A) LENGTH:  10 nucleotides
        (B) TYPE: nucleic acid
        (C) STRANDEDNESS: single-stranded
        (D) TOPOLOGY: linear (ii) MOLECULE TYPE: DNA (iii) HYPOTHETICAL: No (iv) SEQUENCE DESCRIPTION: SEQ ID NO:18 :

CGCGCGCGGA                                                              10

(2) INFORMATION FOR SEQ ID NO:19 :

(i) SEQUENCE CHARACTERISTICS:
        (A) LENGTH:  10 nucleotides
        (B) TYPE: nucleic acid
        (C) STRANDEDNESS: single-stranded
        (D) TOPOLOGY: linear (ii) MOLECULE TYPE: DNA (iii) HYPOTHETICAL: No (iv) SEQUENCE DESCRIPTION: SEQ ID NO:19 :

CGCGCGCGCC                                                              10

(2) INFORMATION FOR SEQ ID NO:20 :

(i) SEQUENCE CHARACTERISTICS:
        (A) LENGTH:  10 nucleotides
        (B) TYPE: nucleic acid
        (C) STRANDEDNESS: single-stranded
        (D) TOPOLOGY: linear (ii) MOLECULE TYPE: DNA (iii) HYPOTHETICAL: No (iv) SEQUENCE DESCRIPTION: SEQ ID NO:20 :

CGCGCGCGCT                                                              10

(2) INFORMATION FOR SEQ ID NO:21 :

(i) SEQUENCE CHARACTERISTICS:
        (A) LENGTH:  10 nucleotides
        (B) TYPE: nucleic acid
```

```
            (C) STRANDEDNESS: single-stranded
            (D) TOPOLOGY: linear (ii) MOLECULE TYPE: DNA (iii) HYPOTHETICAL: No (iv) SEQUENCE DESCRIPTION: SEQ ID NO:21 :

CGCGCGCGCU                                                              10

(2) INFORMATION FOR SEQ ID NO:22 :

(i) SEQUENCE CHARACTERISTICS:
            (A) LENGTH:  10 nucleotides
            (B) TYPE: nucleic acid
            (C) STRANDEDNESS: single-stranded
            (D) TOPOLOGY: linear (ii) MOLECULE TYPE: DNA (iii) HYPOTHETICAL: No (iv) SEQUENCE DESCRIPTION: SEQ ID NO:22 :

CGCGCGCGTT                                                              10

(2) INFORMATION FOR SEQ ID NO:23 :

(i) SEQUENCE CHARACTERISTICS:
            (A) LENGTH:  10 nucleotides
            (B) TYPE: nucleic acid
            (C) STRANDEDNESS: single-stranded
            (D) TOPOLOGY: linear (ii) MOLECULE TYPE: DNA (iii) HYPOTHETICAL: No (iv) SEQUENCE DESCRIPTION: SEQ ID NO:23 :

CGCGCGCGTC                                                              10

(2) INFORMATION FOR SEQ ID NO:24 :

(i) SEQUENCE CHARACTERISTICS:
            (A) LENGTH:  10 nucleotides
            (B) TYPE: nucleic acid
            (C) STRANDEDNESS: single-stranded
            (D) TOPOLOGY: linear (ii) MOLECULE TYPE: DNA (iii) HYPOTHETICAL: No (iv) SEQUENCE DESCRIPTION: SEQ ID NO:24 :

CGCGCGCGTU                                                              10

(2) INFORMATION FOR SEQ ID NO:25 :

(i) SEQUENCE CHARACTERISTICS:
            (A) LENGTH:  10 nucleotides
            (B) TYPE: nucleic acid
            (C) STRANDEDNESS: single-stranded
            (D) TOPOLOGY: linear (ii) MOLECULE TYPE: DNA (iii) HYPOTHETICAL: No (iv) SEQUENCE DESCRIPTION: SEQ ID NO:25 :

CGCGCGCGUC                                                              10
```

(2) INFORMATION FOR SEQ ID NO:26 :

(i) SEQUENCE CHARACTERISTICS:
        (A) LENGTH:  10 nucleotides
        (B) TYPE: nucleic acid
        (C) STRANDEDNESS: single-stranded
        (D) TOPOLOGY: linear (ii) MOLECULE TYPE: DNA (iii) HYPOTHETICAL: No (iv) SEQUENCE DESCRIPTION: SEQ ID NO:26 :

CGCGCGCGUT                                                        10

(2) INFORMATION FOR SEQ ID NO:27 :

(i) SEQUENCE CHARACTERISTICS:
        (A) LENGTH:  10 nucleotides
        (B) TYPE: nucleic acid
        (C) STRANDEDNESS: single-stranded
        (D) TOPOLOGY: linear (ii) MOLECULE TYPE: DNA (iii) HYPOTHETICAL: No (iv) SEQUENCE DESCRIPTION: SEQ ID NO:27 :

CGCGCGCGUU                                                        10

(2) INFORMATION FOR SEQ ID NO:28 :

(i) SEQUENCE CHARACTERISTICS:
        (A) LENGTH:  18 nucleotides
        (B) TYPE: nucleic acid
        (C) STRANDEDNESS: single-stranded
        (D) TOPOLOGY: linear (ii) MOLECULE TYPE: DNA (iii) HYPOTHETICAL: No (iv) SEQUENCE DESCRIPTION: SEQ ID NO:28 :

CACACACACA CACACAAA                                            18

(2) INFORMATION FOR SEQ ID NO:29 :

(i) SEQUENCE CHARACTERISTICS:
        (A) LENGTH:  18 nucleotides
        (B) TYPE: nucleic acid
        (C) STRANDEDNESS: single-stranded
        (D) TOPOLOGY: linear (ii) MOLECULE TYPE: DNA (iii) HYPOTHETICAL: No (iv) SEQUENCE DESCRIPTION: SEQ ID NO:29 :

CACACACACA CACACAGA                                            18

(2) INFORMATION FOR SEQ ID NO:30 :

(i) SEQUENCE CHARACTERISTICS:
        (A) LENGTH:  18 nucleotides
        (B) TYPE: nucleic acid
        (C) STRANDEDNESS: single-stranded
        (D) TOPOLOGY: linear (ii) MOLECULE TYPE: DNA (iii) HYPOTHETICAL: No (iv) SEQUENCE DESCRIPTION: SEQ ID NO:30 :

CACACACACA CACACACC                                                          18

(2) INFORMATION FOR SEQ ID NO:31 :

(i) SEQUENCE CHARACTERISTICS:
            (A) LENGTH:  18 nucleotides
            (B) TYPE: nucleic acid
            (C) STRANDEDNESS: single-stranded
            (D) TOPOLOGY: linear (ii) MOLECULE TYPE: DNA (iii) HYPOTHETICAL: No (iv) SEQUENCE DESCRIPTION: SEQ ID NO:31 :

CACACACACA CACACACT                                                          18

(2) INFORMATION FOR SEQ ID NO:32 :

(i) SEQUENCE CHARACTERISTICS:
            (A) LENGTH:  18 nucleotides
            (B) TYPE: nucleic acid
            (C) STRANDEDNESS: single-stranded
            (D) TOPOLOGY: linear (ii) MOLECULE TYPE: DNA (iii) HYPOTHETICAL: No (iv) SEQUENCE DESCRIPTION: SEQ ID NO:32 :

CACACACACA CACACACU                                                          18

(2) INFORMATION FOR SEQ ID NO:33 :

(i) SEQUENCE CHARACTERISTICS:
            (A) LENGTH:  18 nucleotides
            (B) TYPE: nucleic acid
            (C) STRANDEDNESS: single-stranded
            (D) TOPOLOGY: linear (ii) MOLECULE TYPE: DNA (iii) HYPOTHETICAL: No (iv) SEQUENCE DESCRIPTION: SEQ ID NO:33 :

CACACACACA CACACATT                                                          18

(2) INFORMATION FOR SEQ ID NO:34 :

(i) SEQUENCE CHARACTERISTICS:
            (A) LENGTH:  18 nucleotides
            (B) TYPE: nucleic acid
            (C) STRANDEDNESS: single-stranded
            (D) TOPOLOGY: linear (ii) MOLECULE TYPE: DNA (iii) HYPOTHETICAL: No (iv) SEQUENCE DESCRIPTION: SEQ ID NO:34 :

CACACACACA CACACATC                                                          18

(2) INFORMATION FOR SEQ ID NO:35 :

(i) SEQUENCE CHARACTERISTICS:
            (A) LENGTH:  18 nucleotides
            (B) TYPE: nucleic acid
            (C) STRANDEDNESS: single-stranded
            (D) TOPOLOGY: linear -continued (ii) MOLECULE TYPE: DNA (iii) HYPOTHETICAL: No (iv) SEQUENCE DESCRIPTION: SEQ ID NO:35 :

CACACACACA CACACATU                                                                18

(2) INFORMATION FOR SEQ ID NO:36 :

(i) SEQUENCE CHARACTERISTICS:
        (A) LENGTH:  18 nucleotides
        (B) TYPE: nucleic acid
        (C) STRANDEDNESS: single-stranded
        (D) TOPOLOGY: linear (ii) MOLECULE TYPE: DNA (iii) HYPOTHETICAL: No (iv) SEQUENCE DESCRIPTION: SEQ ID NO:36 :

CACACACACA CACACAUC                                                                18

(2) INFORMATION FOR SEQ ID NO:37 :

(i) SEQUENCE CHARACTERISTICS:
        (A) LENGTH:  18 nucleotides
        (B) TYPE: nucleic acid
        (C) STRANDEDNESS: single-stranded
        (D) TOPOLOGY: linear (ii) MOLECULE TYPE: DNA (iii) HYPOTHETICAL: No (iv) SEQUENCE DESCRIPTION: SEQ ID NO:37 :

CACACACACA CACACAUT                                                                18

(2) INFORMATION FOR SEQ ID NO:38 :

(i) SEQUENCE CHARACTERISTICS:
        (A) LENGTH:  18 nucleotides
        (B) TYPE: nucleic acid
        (C) STRANDEDNESS: single-stranded
        (D) TOPOLOGY: linear (ii) MOLECULE TYPE: DNA (iii) HYPOTHETICAL: No (iv) SEQUENCE DESCRIPTION: SEQ ID NO:38 :

CACACACACA CACACAUU                                                                18